(12) United States Patent
von Bulow et al.

(10) Patent No.: US 6,419,664 B1
(45) Date of Patent: Jul. 16, 2002

(54) DRAINABLE COLLECTION BAG FOR HUMAN BODY WASTES

(75) Inventors: Martin von Bulow; Birthe Vestbo Andersen; Jan Rolin Frederiksen, all of Espergærde; Søren Hansen, Helsingør, all of (DK)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 09/489,905

(22) Filed: Jan. 24, 2000

(30) Foreign Application Priority Data

Oct. 20, 1999 (DK) ........................................ 1999 01507

(51) Int. Cl.[7] .................................................. A61F 5/44
(52) U.S. Cl. ........................ 604/337; 604/317; 604/327; 604/332
(58) Field of Search ................................ 604/327–345, 604/317–326; 383/90

(56) References Cited

U.S. PATENT DOCUMENTS

| | | | |
|---|---|---|---|
| 2,520,831 A | | 8/1950 | Chincholl .................. 128/283 |
| 4,439,191 A | * | 3/1984 | Hogan ........................ 604/332 |
| 4,988,343 A | | 1/1991 | Ballan ........................ 604/332 |
| 5,022,693 A | * | 6/1991 | Loveless ..................... 294/1.1 |
| 5,125,133 A | | 6/1992 | Morrison .................. 24/30.5 R |

FOREIGN PATENT DOCUMENTS

| | | |
|---|---|---|
| GB | 2 000 683 | 1/1979 |
| GB | 2 268 065 | 1/1994 |
| WO | 96/19164 | 6/1996 |
| WO | 99/25278 | 5/1999 |

* cited by examiner

Primary Examiner—John G. Weiss
Assistant Examiner—C L Anderson
(74) Attorney, Agent, or Firm—Jacobson Holman, PLLC

(57) ABSTRACT

In a collecting bag comprising a bag member formed by two film blanks with joined edges and an inlet opening for connection of the bag to a body orifice provided in one of said film blanks, an elongated discharge portion ending in a discharge opening is connected with the bag member, said discharge portion having a width permitting opening and reclosing by manual unfolding and folding operations and defining a narrowed discharge passage for the discharge of more or less entirely liquid body wastes, a substantially free flow through the narrowed discharge passage in the open unfolded condition of the discharge portion and thereby a free discharge flow of the bag content being obtainable by arrangement of a flexible hose member in the discharge passage.

21 Claims, 5 Drawing Sheets

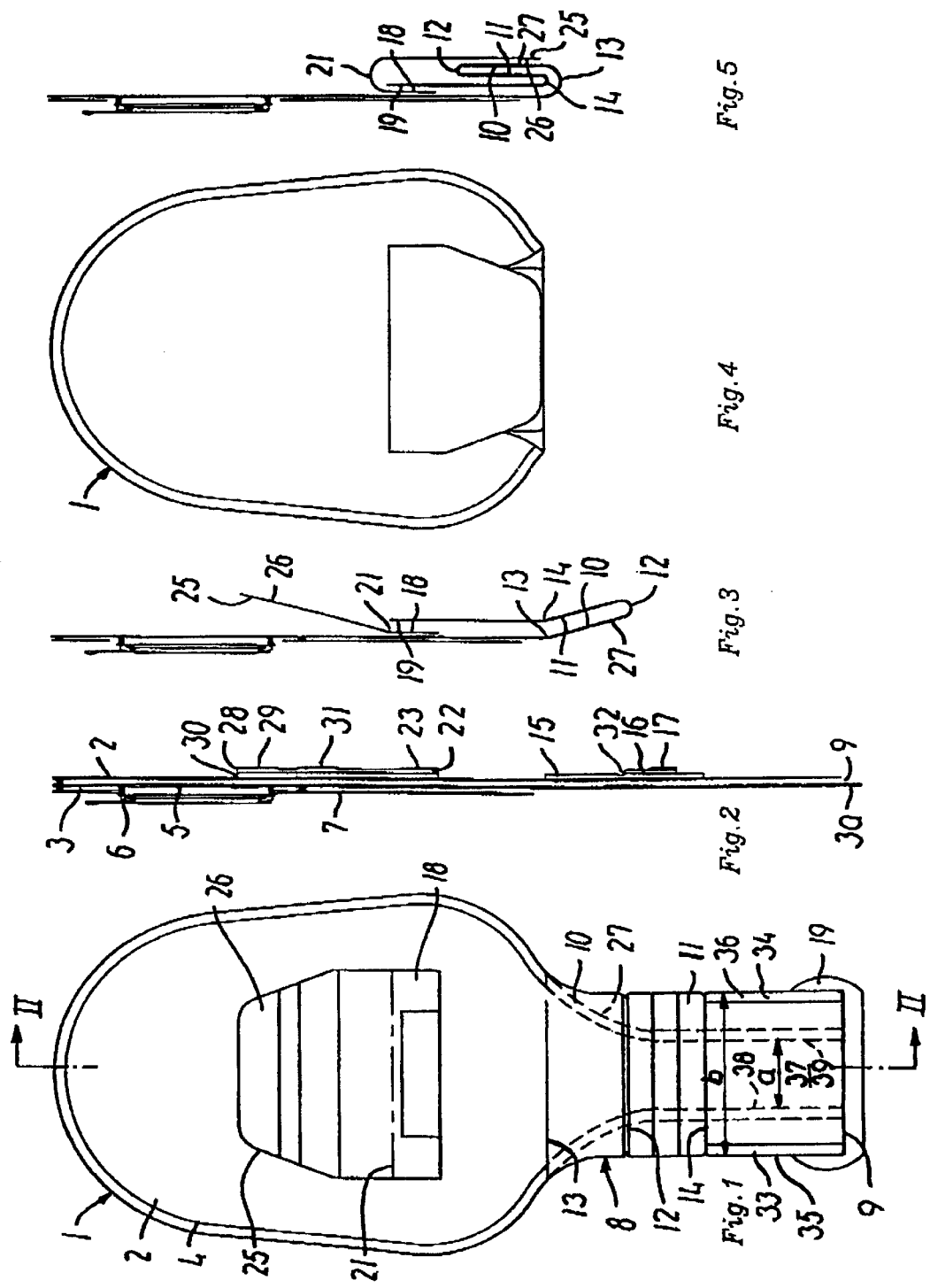

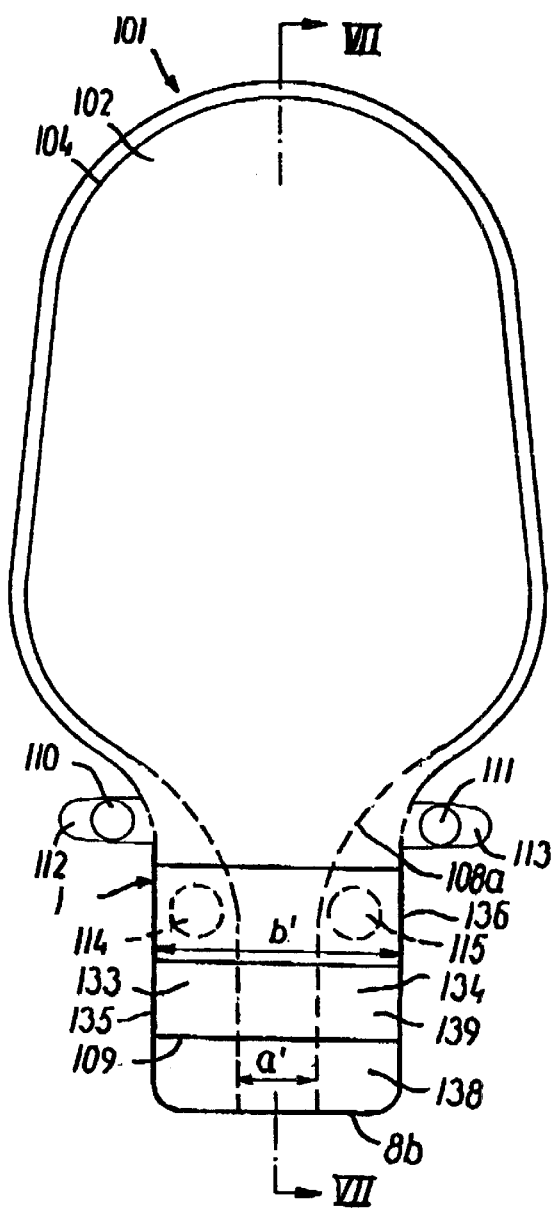
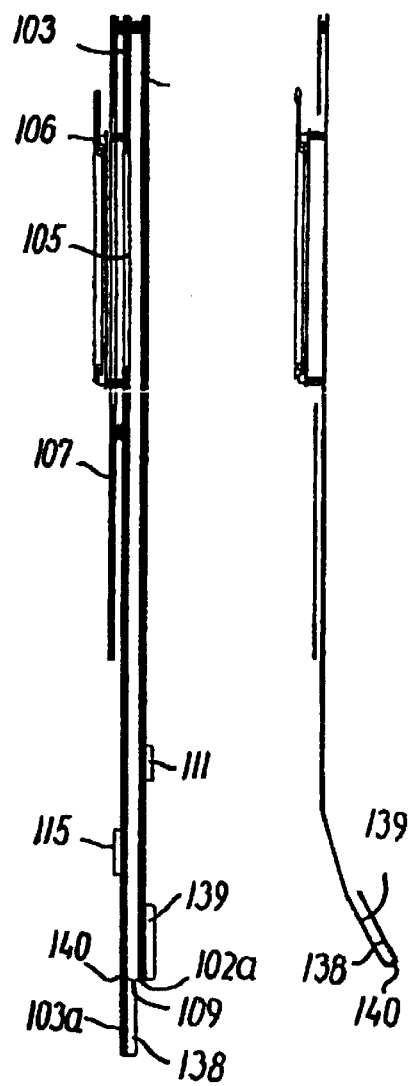
FIG.6   FIG.7   FIG.8

DRAINABLE COLLECTION BAG FOR HUMAN BODY WASTES

CROSS-REFERENCE TO RELATED APPLICATIONS

The present application claims the benefit of priority from Danish patent application No. PA 1999 01507.

The present invention relates to collecting bags for human body wastes and, in particular to a collecting bag of the kind which for draining purposes are formed with a reclosable discharge opening in addition to the inlet opening for connection of the bag to a body orifice.

BACKGROUND OF THE INVENTION

This type of drainable collecting bags are often used as ostomy bags. In the case of ileostomy patients and colostomy patients with uncontrolled release of faeces of a more or less fluid consistence as well as in the case of urostomi patients, the collecting bag has to be emptied rather frequently, and the closure device thus has to be easy to open and re-close after emptying and at the same time provide a reliable and tight seal in operation, ie. between emptyings.

Several different designs of closure devices for ostomy bags have been developed to meet this object and are generally known.

Examples of such prior art closure devices have been disclosed e.g. in U.S. Pat. No. 2,520,831, U.S. Pat. No. 5,125,133, U.S. Pat. No. 4,988,343, WO 96/19164, GB-A-2 000 683 and GB-A-2 268 065.

From published international patent application WO 99/25278 a closure device is known, by which opening and closing of the bag is carrier out in two distinct stages by successive operation of first and second closure means, said distinct stages being separated by the bag occupying an intermediate position in which only the first closure means is activated. The first closure means comprises a first pair of contact surfaces between first and second folding lines and between the first folding line and a limiting line, respectively, which are brought in contact by folding the discharge porion along the first folding line and are maintained in contact in the intermediate position as well as the position of use of the bag. The second closure means comprises a second pair of contact surfaces which are maintained in contact only in the position of use of the bag.

In the first stage of the opening of the bag the second closure means is opened and the discharge portion is directed into the correct position over a toilet or the like with the bag in the intermediate position, whereas in the subsequent second stage the first closure means is opened to achieve a controlled discharge of the bag contents. After the discharge the discharge portion may be closed again in two distinct stages comprising closing of the first closure means followed by the closure of the second closure means, whereby the advantage is achieved that rinsing of the discharge portion after emptying of the bag may be carried out in the intermediate position to remove soiling of the discharge opening cause by the newly discharged body wastes.

Whereas this solution offers essential advantages in respect of easier operation requiring less dexterity and a logical and obvious order of activation/deactivation of the first and second closure means together with an improved security against leakage due to the capability of the first closure means to hold the bag closed in the closed and intermediate positions and the additional leakage protection provided by the second closure means in the closed position, the folding operations needed to bring the discharge portion from the position of use to the opened position via the intermediate position and vice versa requires a certain minimum width of the discharge portion between the outer contours of the joined side edges thereof to enable easy manual operation also in the frequent cases where ostomy patients have significantly reduced dexterity. Typically the width of the discharge portion in its flat condition will be between 60 and 80 mm.

Since in prior art ostomy bags of the type defined the cross-sectional dimension of the discharge passage provided from the interior of the bag through the discharge portion towards the discharge opening at the distal end thereof is defined by seams such as welding seams, adhesive seams or any other suitable type of seams joining the side edges of the discharge portion, the size of the discharge passage will by and large be determined by the minimum width of the discharge portion needed for the purpose of easy folding and unfolding.

Experience with collecting bags of the type defined have shown that, whereas the control of discharge of the bag content when emptying the bag is excellent for the majority of users including ileostomy patients for which the bag content may be relatively thin, the discharge control becomes less satisfactory when the bag content is more or less entirely liquid as is the case for urostomy patients and newly operated ileostomy patients due to the width of the discharge passage.

BRIEF SUMMARY OF THE INVENTION

It is the object of the invention to remedy this inconvenience and provide a significantly improved control of the discharge of liquid or very thin waste fluids when emptying the collection bag is effected, while at the same time offering an external width of the discharge portion sufficient to maintain easy manual operability of the discharge portion by folding.

According to the invention a collection bag for human body wastes is provided, comprising a bag member formed by two film blanks with joined edges, an inlet opening provided in one of said film blanks, connecting elements surrounding said inlet opening for connection of the bag to a body orifice, an elongated discharge portion having a proximal end connected with the bag member at a distance from the inlet opening and a distal end defining a discharge opening, said discharge portion having substantially parallel side edges and a minimum width between said side edges permitting manual folding of the discharge portion in a longitudinal direction thereof along a folding line crossing said discharge portion between said distal and proximal ends to bring the discharge portion from an open unfolded condition to a closed folded condition and vice versa, comprising the improvement that a narrowed discharge passage is formed in said discharge portion between said side edges, said passage having a width less than 60% of said minimum width of the discharge portion.

By narrowing the discharge passage with respect to the total external width of the discharge portion a significantly improved control of the discharge of liquid or very thin waste fluids when emptying the collection bag is effected, while at the same time offering an external width of the discharge portion sufficient to maintain easy manual operability of the discharge portion by folding.

In one embodiment the discharge portion may be formed by two end sections of said film blanks, which are joined along said side edges, and the discharge passage may be defined by seams joining said end sections substantially parallel to said side edges, the distance between said joining seams being more than 10 mm, but less than 60% of the distance between outer contours of said joined side edges of the discharge portion.

By a further implementation of the invention a collection bag of the kind set forth is provided, comprising

- a bag member formed by two film blank with joined edges,
- an inlet opening provided in one of said film blanks,
- connecting elements surrounding said inlet opening for connection of the bag to a body orifice,
- an elongated discharge portion having a proximal end connected with the bag member at a distance from the inlet opening and a distal end defining a discharge opening, said discharge portion having substantially parallel side edges and a minimum width between said side edges permitting manual folding of the discharge portion in a longitudinal direction thereof along a folding line crossing said discharge portion between said distal and proximal ends to bring the discharge portion from an open unfolded condition to a closed folded condition and vice versa,
- comprising the improvement that
- a narrowed discharge passage is formed in said discharge portion between said side edges, said passage having a width less than 60% of said minimum width of the discharge portion, said discharge passage being substantially tubular in said open unfolded condition of the discharge portion.

BRIEF DESCRIPTION OF THE SEVERAL VIEWS OF THE DRAWINGS

In the following the invention will be described in further detail with reference to the accompanying schematic drawings, in which FIG. 1 shows a plane view of a first embodiment of a collecting bag according to the invention, seen from the side intended to face away from the user and in the fully open position;

FIG. 2 shows a longitudinal section of the collecting bag along the line II—II in FIG. 1;

FIG. 3 is a schematic side view diagram of the collecting bag in an intermediate position showing only relevant parts of the bag;

FIG. 4 is a view corresponding to FIG. 1 in the fully closed position of the bag;

FIG. 5 is a diagram corresponding to FIG. 3 of the collecting bag in the fully closed position;

FIGS. 6 to 10 are views corresponding to FIGS. 1 to 5, respectively, of a second embodiment of a collecting bag according to the invention.

DETAILED DESCRIPTION

Figure 9:
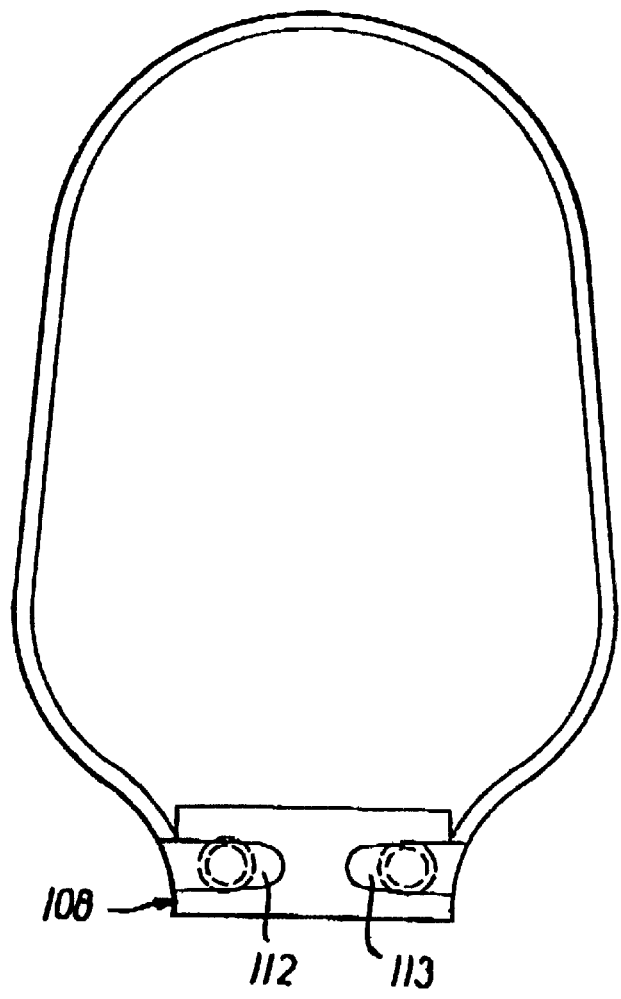
Figure 10:
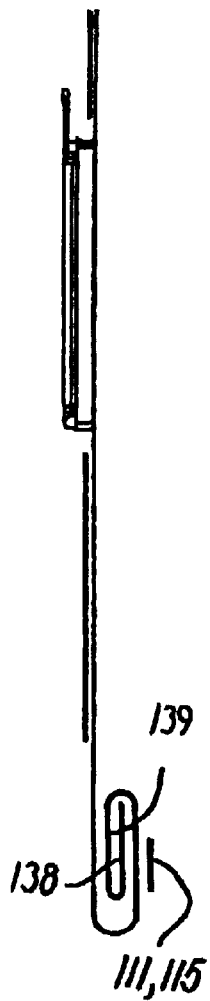

The collecting bag shown in FIGS. 1 to 5 is designed as an ostomy bag of a common type known per se. With reference to the first embodiment shown in FIGS. 1 to 5 of the drawings, the collecting bag comprises a bag member 1 formed by two film blanks 2,3 which are joined along their edges by means of a seam 4 made by welding or in any other convenient manner. The film blanks may be made from any suitable flexible plastic sheet or foil material.

In the film blank 3 which in use is intended to face the user and thus forms the back wall of the bag, an inlet opening 5 is provided which in a manner known per se is surrounded by connecting elements 6 for connection of the bag to a body orifice, ie. in this case an intestinal orifice in the form of a so-called stoma in the user's abdominal wall.

In the figures, the connecting elements 6 are shown as parts of a coupling system, but alternatively use may also be made of a single connecting element comprising an annular adhesive disc for direct adhesion to the user's skin.

As most clearly seen in FIG. 2 a comfort layer 7 of another material than the one used for the film blanks is provided on the back film blank 3.

At a distance from the inlet opening 5, the bag is designed with a narrowed, elongated discharge portion 8 starting at a proximal or neck end and extending to a distal or terminal end. The discharge portion 8 is formed by two end sections of the film blanks 2,3 and is likewise joined along its side edges by substantially parallel welding seams 33 and 34 extending along the external contours 35 and 36 of the side edges. In the embodiment shown the width of the discharge portion 8 in its flat condition defined by the distance b between the outer contours 35 and 36 may be between 60 and 80 mm, e.g. 65 mm.

In the vicinity of the distal end of the discharge portion, a discharge opening 9 through which the bag may be emptied of its contents is formed by the slit between the end edges of the two film blanks 2,3.

According to the invention a narrowed discharge passage 37 is defined in the discharge portion 8 by two separate welding seams 38 and 39 extending substantially parallel to and inside the side edge contours 35 and 36. The discharge passage 37 is dimensioned such with respect to the overall width of the discharge portion 8 that distance a of the welding seams 38 and 39 defining the width of the discharge passage 37 in the flat foldable condition of the discharge portion 8 is less than 60% of the distance b between the outer contours 35 and 36 of the side edges of the discharge portion 8. In the embodiment shown in FIGS. 1 to 5. in which the walls of the narrowed discharge passage are formed by the end sections of film blanks 2 and 3, a free discharge flow of the bag content through the narrowed discharge passage after the discharge portion is brought from its closed folded condition into its open unfolded condition, as further described in the following, is ensured by dimensioning the distance a to be more than 10 mm, For an overall width of the discharge portion 8 as defined by the distance b between 60 and 80 mm the distance a between the welding seams 38 and 39 may typically be between 15 and 36 mm, e.g. 25 mm.

In order to bring the bag from the open or discharge position shown in FIGS. 1 and 2 to a position of use, in which the bag is closed, the collecting bag comprises a closure device as described in WO 99/25278, the disclosure of which is incorporated herein by reference.

In the embodiment shown in FIGS. 1 to 5 this closure device comprises at the proximal end of the discharge portion 8 a first closure means with a pair of contact surfaces 10,11, one extending between first and second folding lines 12 and 13, and the other between the first folding line 12 and a limiting line 14. The one contact surface 10 is entirely provided on a carrier plate 15 which is fastened to the front film blank 2. The carrier plate 15 extends further past the first folding line 12 in the direction towards the discharge opening 9. Here, on the other contact surface 11, the carrier plate is covered by a layer of adhesive 16 which is capable of repeated adhesion and is preferably washable. The carrier plate 15 itself is made from a foam material but may also be made from any other suitable material, such as a plastic or a fibre material, and contributes to the tight seal of the closure.

In a first stage of closing the bag, the discharge portion 8 is folded along the first folding line 12, whereby the contact surfaces 10,11 of the first pair are brought into contact and are held in this position by the layer of adhesive 16. In order to ease this folding operation, the carrier plate 15 is provided with a notch 32 substantially extending along the first folding line 12, or the contact surfaces 10,11 may be provided on separate carrier plates with a spacing between them.

The layer of adhesive 16 on the other contact surface 11 is partly covered by a cover layer 17 in order to facilitate subsequent release of the adhesive contact. To obtain optimum closure function the size and position of the layer of adhesive 16 and/or the cover layer 17 may be varied, just as the strength of the adhesive may be varied. The layer of adhesive 16 may as well be provided on the contact surface 10 between the first and second folding lines 12,13, or on both of these surfaces. By providing the layer of adhesive only on the contact surface 10, cleaning of the discharge portion is facilitated, however, as it is possible to squeeze and rinse the discharge portion 8 all the way from the distal end to the first folding line 12 without coming into contact with the adhesive layer.

Following this first closing stage, after which the bag is in an intermediate position, the distal end of the discharge portion 8 is closed by a second closure means.

The second closure means comprises a second pair of contact surfaces 18,19, one of which 18 is provided on a flap element fastened to the front film blank 2 in a lower portion up to a third folding line 21. The upper portion of the flap element is formed as a flap 25. The function of the flap 25 will be described below. The contact surface 18 extends from the end edge of the flap element facing the discharge portion 8 up to the third folding line 21 which is placed at a distance from the first folding line 12 substantially corresponding to the distance between the first folding line 12 and the distal end of the discharge portion 8. At the distal end, the other contact surface 19 of the second pair is provided, partly on the front film blank 2, partly on an extended portion 3a of the back film blank 3 shown most clearly in FIG. 2.

In the position of the bag shown in FIG. 3, the two contact surfaces 18,19 are brought into contact with each other and are held in this position by an adhesive layer 22 on the contact surface 18 on the flap element. A cover layer 23 on the contact surface 18 provides a substantially U-shaped adhesive surface in order to facilitate the subsequent release of the adhesive contact. Just as the adhesive layer 16 on the first pair of contact surfaces, the adhesive layer 22 is capable of repeated adhesion and may also be washable.

From the position shown in FIG. 3, the discharge portion 8 is in again folded on to the bag member 1 along the second folding line 13 and the limiting line 14 which in this position overlies the second folding line 13. Subsequently, the flap 25 is folded along the third folding line 21 so that a contact surface 26 on the flap 25 is brought into contact with another contact surface 27 constituting the other part of a third pair positioned on the back film blank 3 opposite the contact surface 10 of the first pair situated between the first and second folding lines 12,13 on the front film blank 2. To this end, the contact surface 26 on the flap 25 is covered by a layer of adhesive 28 which is capable of repeated adhesion and which may be washable. A cover layer 29 covering the outermost part of the flap 25 provides for easier opening of the collecting bag as the flap 25 may be simply lifted in order to release the contact between the contact surfaces 26,27. As shown in FIGS. 2 and 7, the adhesive layers 22 and 28 may be formed integrally on a carrier plate 30 extending throughout the flap element and which may be made from foam, plastic or fibre material. In order to further facilitate the lifting of the flap 25, a cover layer 31 covers the area of the flap below the contact surface 26 in the first embodiment. The same considerations regarding the size and position of the layers of adhesive and the cover layers, and the strength of the adhesive used, apply to the second and third pairs of contact surfaces.

The collecting bag is now in the position of use shown in FIGS. 4 and 5. As the discharge portion 8 is entirely folded on to the bag member 1, it does not contribute to the outer contour of the bag member, thus providing a very compact design of the collecting bag. It is also noted that during operation of the bag, when the contents exert a pressure on the first closure means, the contact between the first pair of contact surfaces 10,11 is tightened additionally from the contact between the contact surface 26 on the flap 25 and the other contact surface 27 on the discharge portion 8 itself.

When the collecting bag has been in use for some time and is at least partly filled, the bag is opened in a series of operations.

First, the adhesive contact between the third pair of contact surfaces 26,27 is released by lifting the flap 25 and unfolding it along the third folding line 21. The second closure means is now deactivated by pulling said one contact surface 19 of the second pair on the distal end of the discharge portion 8 out of contact with the other contact surface 18 on the flap element. Subsequently, the discharge portion 8 is unfolded and an intermediate position has been reached. It is noted that the contents of the bag are still prevented from flowing out by means of the first closure means which is still active. Only when the distal part of the discharge portion 8 has been directed into a suitable position, eg. over a toilet, the first closure means is deactivated by a pull in the distal end of the discharge portion, whereby the bag assumes its open position shown in FIGS. 1 and 6, respectively, and its contents are allowed to flow out of the bag.

Subsequently, the user may squeeze the remaining contents out of the bag by stroking or massaging movements in the direction towards the discharge opening 9. When the bag has been emptied, the discharge portion 8 may be thoroughly rinsed.

Eventually, the collecting bag may be closed by following the procedure described in the above.

In FIGS. 6 to 10 a further embodiment of the collection bag according to the invention is shown, which is likewise designed as an ostomy bag of a generally known and common type and comprises a bag member 101 formed by two film blanks 102,103 which are joined along their edges by means of a seam 104 made by welding or in any other convenient manner. The film blanks may be made from any suitable flexible plastic sheet or foil material.

In the film blank 103 which in use is intended to face the user and thus forms the back wall of the bag, an inlet opening 105 is provided which in a manner known per se is surrounded by connecting elements 106 for connection of the bag to a body orifice, ie. in this case an intestinal orifice in the form of a so-called stoma in the user's abdominal wall.

Like in FIGS. 1 to 5, the connecting elements 6 are shown as parts of a coupling system, but alternatively use may also be made of a single connecting element comprising an annular adhesive disc for direct adhesion to the user's skin.

As seen in FIG. 7 a comfort layer 107 of another material than the one used for the film blanks may be provided on the back film blank 103. Alternatively, both of the two film blanks may be provided with such a comfort layer which may be made of a conventional non-woven tissue material.

At a distance from the inlet opening 105, the bag is designed with a narrowed, elongated discharge portion 108 starting at a proximal or neck end 108a and extending to a distal or terminal end 108b. The discharge portion 108 is formed by two end sections of the film blanks 102,103 and is likewise joined by welding seams 133 and 134 extending along the outer contours 135, 136 of the parallel opposed side edges of the discharge portion 108. Also in this embodiment the width of the discharge portion 108 in its flat condition defined by the distance b' between the outer contours 135 and 136 may be between 60 and 80 mm, e.g. 65 mm.

In the vicinity of the distal end 108b of the discharge portion 108, a discharge opening 109, through which the bag may be emptied of its contents, is formed between the two film blanks 102, 103.

Also in this embodiment a narrowed discharge passage 137 is defined in the discharge portion 108, but contrary to the embodiment shown in FIGS. 1 to 5 the narrowed discharge passage 137 is provided by increasing the width of welding seams 133 and 134, such that the distance a' of the welding seams 133 and 134 defining the width of the discharge passage 137 in the flat foldable condition of the discharge portion 108 is more than 10 mm, but less than 60% of the distance b' between the outer contours 135 and 136 of the side edges of the discharge portion 108. In the embodiment shown the width of the discharge passage 137 in the flat condition of the discharge portion 108 defined by the distance a' between the welding seams 133 and 134 may be between 15 and 36 mm, e.g. 25 mm.

In order to bring the bag from the open or discharge position shown in FIGS. 1 and 2 to a position of use, in which the bag is closed, the collecting bag comprises a locking device which in the embodiment shown comprises foldable locking strips 112 and 113 projecting from the side edge contours 135 and 136 of the discharge portion 108 at the proximal end 108a thereof. The projecting foldable locking strips 112 and 113 which may be formed integrally with one of the film blanks 102,103 are provided with a first set of locking means 110 and 111, which may comprise male snap fastening members, VELCRO closure members, different types of adhesive members etc. and are releasably engageable with a second set of mating locking means 114 and 115 provided on the back film blank 103. It should be noted that the locking device may be designed in other ways, e.g. as described in applicant's co-pending Danish patent application No. PA 1998 00805, or as a traditional locking clip.

A resilient seal member in the form of a compressible sealing plate 138 is provided on an extension 103a of the back film blank 103 and the front film blank 102 is at its end portion provided with a similar resilient seal member, likewise in the form of a sealing plate 139. The sealing plates 138,139 are made from a suitable resilient material, eg. foam, and have a greater rigidity than the film blanks 102 and 103 and extend throughout the width of the discharge portion 108 on either side of the discharge opening 109 which is formed between the extension 103a of film blank 103 and a distal end edge 102a of film blank 102.

In the embodiment shown the sealing plates 138 and 139 have the same generally rectangular shape and are arranged with first longitudinal side edges of the two sealing plates facing each other in substantial parallel relationship with a clearance 140 depending on the resilience or compressibility characteristics of the sealing plate and the tensional strength and strechtability of the film blanks on which the sealing plates are arranged.

When closing the bag, the discharge portion 108 is folded starting from the distal end by initially folding the sealing plate 139 against the sealing plate 138 using the clearance 140 between them as folding line. This initial folding will cause compression of the sealing plates 138 and 139 at least in the parts adjacent the clearance or folding line 140 assisted by the tension of the film blanks 102 and 103 in the folding area, whereby an effectively sealed closure of the discharge opening 109 is provided.

Subsequently, following this initial folding the discharge portion 108 is folded in the embodiment shown two more times until the locking means 114 and 115 are brought into alignment with the projecting locking strips 112 and 113 which are then folded to bring the locking means 110 and 111 into engagement with locking means 114,115.

By using sealing plates 138, 139 made from a compressible resilient material such as foam, the initial folding of the discharge portion 108 at the discharge opening 109 provides for an improved tightness. Due to the compressibility of the foam material in combination with the squeezing effect from the film material in blanks 102 and 103, particles present in the discharge portion are prevented from moving towards the discharge opening, where such particles might cause formation of flow paths which in turn may give rise to leakage from the bag.

In the embodiment shown, there is a resilient seal member on each film blank and one of these, viz. sealing plate 138, is provided on the extension 103a of the back film blank 103, such that the resilient members are positioned substantially in extension of each other. This arrangement provides for an optimum functionality of the collecting bag, but other arrangements including the use of only one resilient seal member on only one of the film blanks to engage with a non-resilient contact surface on the other film blank are also conceivable.

When the collecting bag has been in use for some time and is at least partly filled, the bag may be opened by releasing the locking means 110,111 and 114,115 from their mutual engagement, following which the discharge portion 108 may be unfolded and its distal part may be directed into a suitable position, eg. over a toilet. During this operation, the discharge opening 109 may still be maintained in a sealed condition by pressing the sealing plates 138,139 together. The bag now assumes its open position as shown in FIG. 1 and by releasing the pressure on the sealing plates its contents may be allowed to flow out of the bag.

Subsequently, the user may squeeze the remaining contents out of the bag by stroking or massaging movements in the direction towards the discharge opening 109. When the bag has been emptied, the discharge portion 8 may be thoroughly rinsed.

If desired, the collecting bag may then be closed again by following the closing procedure described in the above.

Figure 11:
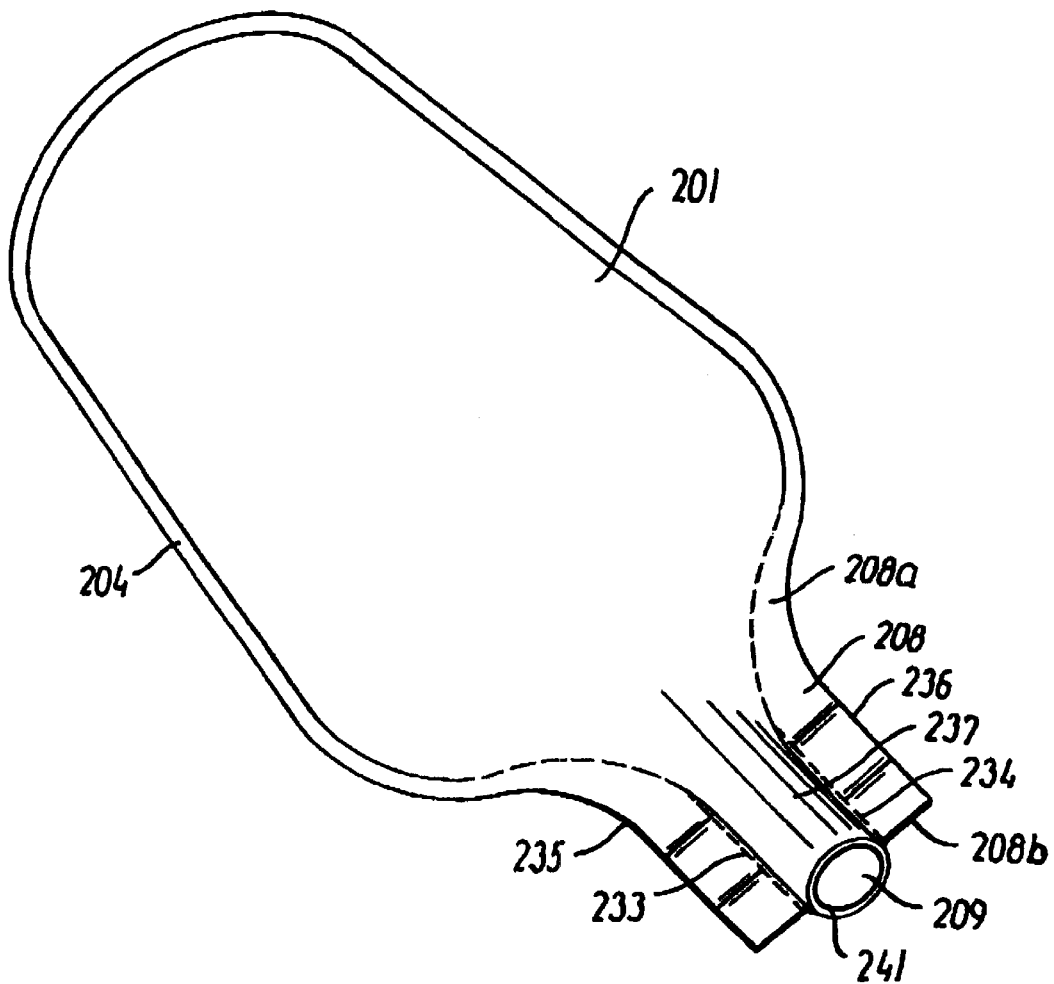
FIGS. 11 and 12 are perspective views of two alternative embodiments of the invention.
Figure 12:
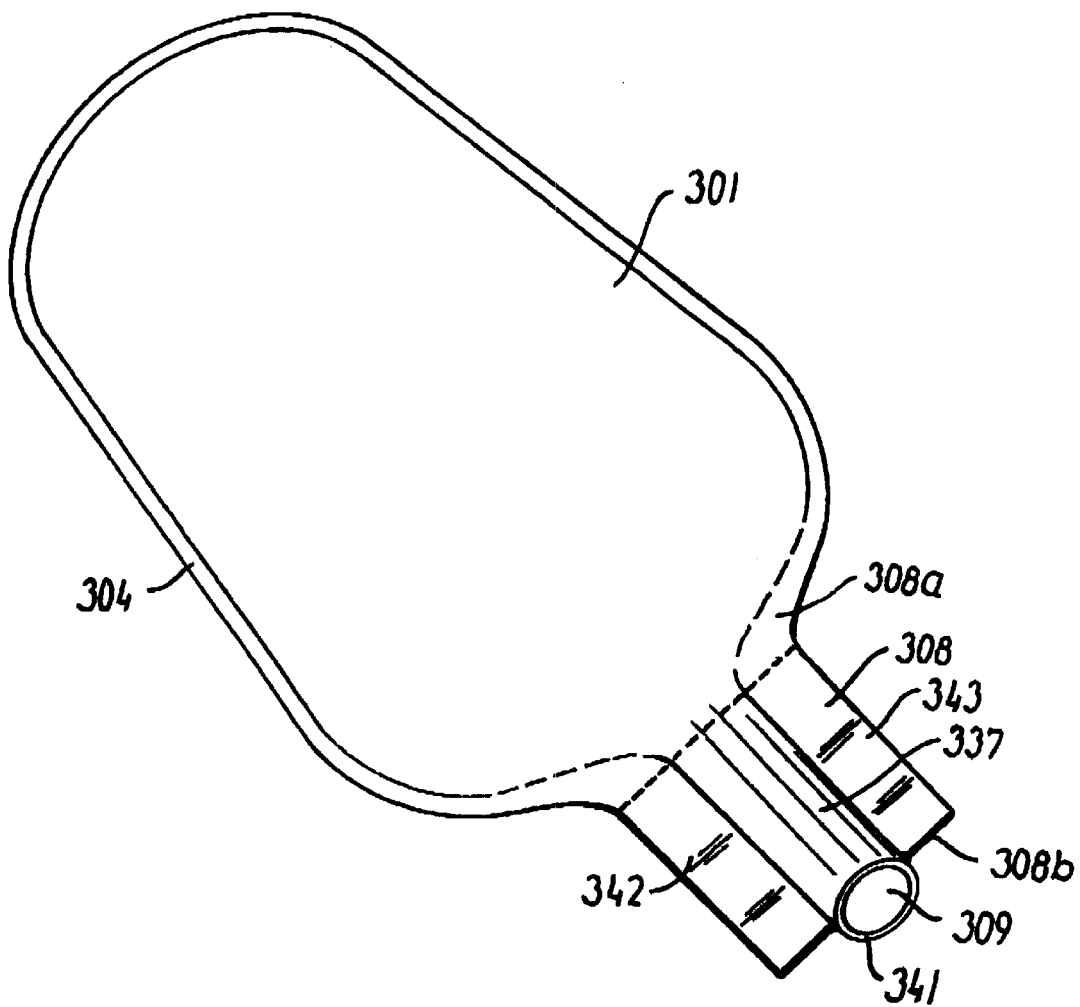

In the perspective views in FIGS. 11 and 12 alternative embodiments are shown. comprising a bag member 201 and 301, respectively, which may be of the same general structure as described for the embodiments of the previous figures by being formed by two film blanks joined along their edges by means of a seam 204 and 304, respectively, made by welding or any other convenient manner.

In one film blank of the bag member 201 or 301 an inlet opening, not illustrated is provided in the same manner as described in the foregoing, and, at a distance from the inlet opening the bag member 201 or 301 continues in a narrowed elongate discharge portion 208 and 308, respectively, which at a proximal or neck end 208a and 308a, respectively, is connected with the bag member 201 or 301 and extends to a distal or terminal end 208b and 308b, respectively, at which an opening 209 and 309, respectively, of a narrowed discharge passage 237 and 337, respectively, is formed.

Compared to the embodiments of the previous figures the discharge passage 237, 337 of the embodiments in FIGS. 11 and 12 are formed, however, to be substantially tubular in the open condition of the discharge portion 208. By ensuring a substantially tubular form of the narrowed drainage passage 237, 337 in the open unfolded condition of the discharge portion 208, 308 the perceived need for the embodiments in FIGS. 1 to 10 of a minimum width of the narrowed discharge passage of more than 10 mm may be avoided and the drainage of the bag is made further expedient and convenient by enabling a standard hose connector to be easily fitted within the discharge passage 237 or 337.

In FIG. 11 the discharge portion 208 is formed in the same way as described for the embodiments of the previous figures by integral end sections of the same film blanks, from which the bag member 201 is formed, and the narrowed discharge passage 237 is defined by welding seams 233 and 234, parallel to the outer contours 235 and 236 of the side edges of the discharge portion 208. The substantially tubular form of the discharge passage 237 in the open condition of the discharge portion 208 is obtained by arrangement of a suitable core member between the film blanks of the end sections at the discharge portion 208 at least during the welding of seams 233 and 234. In the embodiment of FIG. 11, in which the walls of the narrowed discharge passage 237 are formed by the end section of the film blanks forming the bag walls, it is preferred to use a core member in the form of a short piece 241 of a flexible hose member of an elastomeric thermoplastic polymer, which could be selected from one or more polystyrene polyethylene/butylene polystyrene copolymers. Such an elastic hose member could remain in the discharge passage after completion of the welding to secure the substantially tubular form of the discharge passage 237 in the open condition of the discharge portion 208, while still allowing folding of the discharge portion 208 to its closed condition.

In the embodiment illustrated in FIG. 12 the discharge portion 308 is a separate member connected with the bag member 301 by welding or in any other convenient manner.

The discharge portion 308, in which the tubular discharge passage 337 is positioned between and integral with side members 342 and 343 providing the width of the discharge portion 308 needed for easy manual folding and unfolding as described above, may preferably be formed by injection moulding of a suitable elastic thermoplastic polymer which could selected from one or more polystyrene polyethylene/butylene polystyrene copolymers.

The wall thickness of the separate discharge portion 308 should be dimensioned to ensure the substantially tubular form of the discharge passage 337 in the open discharge condition, while still allowing the discharge portion 308 to be easily folded into its closed condition. It may be preferred also in this embodiment to arrange a short flexible hose member 341 of an elastomeric thermoplastic material in the discharge passage to ensure proper functionality.

What is claimed is:

1. A collecting bag for human body wastes comprising
   a bag member formed by two film blanks with joined edges,
   an inlet opening provided in one of said film blanks,
   connecting elements surrounding said inlet opening for connection of the bag to a body orifice,
   an elongated discharge portion having a proximal end connected with the bag member at a distance from the inlet opening and a distal end defining a discharge opening, said discharge portion having substantially parallel side edges and a minimum width between said side edges permitting manual folding of the discharge portion in a longitudinal direction thereof along a folding line crossing said discharge portion between said distal and proximal ends to bring the discharge portion from an open unfolded condition to a closed folded condition and vice versa,
   comprising the improvement that
   a narrowed discharge passage is formed in said discharge portion between said side edges, said passage having a width less than 60% of said minimum width of the discharge portion.

2. A collection bag as claimed in claim 1, wherein
   a closure device is arranged at the discharge portion for opening and closing of the bag in two distinct stages by successive operation of first and second closure means in a position of use of the collection bag, said distinct stages being separated by the bag occupying an intermediate position, in which only the first closure means is activated,
   the first closure means comprising a first pair of contact surfaces between a first folding line and a second folding line, and the first folding line and a limiting line, respectively, said contact surfaces being brought into contact by folding the discharge portion along said first folding line and being held in this position in the intermediate position and the position of use of the bag,
   said first pair of contact surfaces being provided on at least one carrier plate fastened to one of the film blanks.

3. A collection bag as claimed in claim 1, wherein at least one resilient seal member having greater rigidity than the discharge portion is attached to one side of the discharge portion at or near the discharge opening to engage a contact surface of the other side of the discharge portion to close the discharge opening in connection with said manual folding.

4. A collection bag as claimed in claim 1, wherein a locking device is provided at the discharge portion for locking the bag in said closed folded condition of the discharge portion.

5. A collection bag as claimed in claim 4, characterized in that said locking device comprises foldable locking strips projecting from said substantially parallel side edges of the discharge portion and being provided at one surface with first locking means engageable with second locking means provided on a surface part of said discharge portion which, after said manual folding, is located in alignment with said locking strips.

6. A collection bag as claimed in claim 1, wherein said minimum width of the discharge portion is between 60 and 80 mm, and the width of the discharge passage is less than 30 mm.

7. A collection bag as claimed in claim 1, wherein said discharge portion is formed by two end sections of said film blanks, said end sections being joined along said side edges, said discharge passage being defined by seams joining said end sections substantially parallel to said side edges, the distance between said seams defining said discharge portion being more than 10 mm, but less than 60% of the distance between outer contours of said side edges of said end sections.

8. A collection bag as claimed in claim 7, wherein said seams defining the discharge passage are separate from welding seams joining the side edges of the discharge portion.

9. A collection bag as claimed in claim 7, wherein the side edges of the discharge portion are joined by substantially parallel seams which also define the discharge passage.

10. A collection bag as claimed in claim 7, wherein said seams defining the discharge passage are welding seams.

11. A collection bag for human body wastes comprising
a bag member formed by two film blank with joined edges,
an inlet opening provided in one of said film blanks,
connecting elements surrounding said inlet opening for connection of the bag to a body orifice,
an elongated discharge portion having a proximal end connected with the bag member at a distance from the inlet opening and a distal end defining a discharge opening, said discharge portion having substantially parallel side edges and a minimum width between said side edges permitting manual folding of the discharge portion in a longitudinal direction thereof along a folding line crossing said discharge portion between said distal and proximal ends to bring the discharge portion from an open unfolded condition to a closed folded condition and vice versa,
comprising the improvement that
a narrowed discharge passage is formed in said discharge portion between said side edges, said passage having a width less than 60% of said minimum width of the discharge portion, said discharge passage being substantially tubular in said open unfolded condition of the discharge portion.

12. A collection bag as claimed in claim 11, wherein said discharge portion is formed by two end sections of said film blanks, said end sections being joined along said side edges, said substantially tubular discharge passage being defined by seams joining said end sections substantially parallel to said side edges.

13. A collection bag as claimed in claim 12, wherein said discharge passage is formed by arrangement of a core member between said end sections at least during welding of said parallel seams.

14. A collection bag as claimed in claim 13, wherein said core member is a flexible hose member.

15. A collection bag as claimed in claim 14, wherein said hose member is made of an elastomeric thermoplastic material.

16. A collection bag as claimed in claim 14, wherein said hose member remains in said discharge passage after said welding.

17. A collection bag as claimed in claim 11, wherein the discharge portion is formed as a separate member connected with the bag member.

18. A collection bag as claimed in claim 17, wherein the discharge portion is formed by injection moulding of an elastomeric thermoplastic polymer.

19. A collection bag as claimed in claim 18, wherein said polymer is selected from one or more of polystyrene, polyethylene/butylene, and polystyrene copolymers.

20. A collection bag as claimed in claim 17, wherein a flexible hose member is arranged in said discharge passage.

21. A flexible hose member as claimed in claim 20, wherein said hose member is made of an elastomeric thermoplastic material.

* * * * *